United States Patent [19]

Balani et al.

[11] Patent Number: 5,364,776
[45] Date of Patent: Nov. 15, 1994

[54] METHOD OF HYDROXYLATING 3-[3-(5-ETHYL-2-METHOXY-6-METHYL-PYRIDYL)METHYL]AMINO-5-ETHYL-6-METHYL-2(1H)-PYRIDINONE WITH LIVER SLICES

[75] Inventors: Suresh K. Balani, Hatfield; Laura R. Kauffman, Jeffersonville; Anthony D. Theoharides, Lansdale, all of Pa.

[73] Assignee: Merck & Co., Inc., Rahway, N.J.

[21] Appl. No.: 841,262

[22] Filed: Feb. 24, 1992

Related U.S. Application Data

[63] Continuation of Ser. No. 771,676, Oct. 4, 1991, abandoned.

[51] Int. Cl.$^5$ .............................................. C12P 17/14
[52] U.S. Cl. ..................................... 435/118; 435/122
[58] Field of Search ............................. 435/118, 122

[56] References Cited

U.S. PATENT DOCUMENTS 5,202,243  4/1993  Balani ............................. 435/118

OTHER PUBLICATIONS

Ratner, L. et al., "Complete nucleotide sequence of the AIDS virus, HTLV-III," Nature 313, 277 (1985).
Toh, H. et al., "Close structural resemblance . . . ," EMBO Journal 4, 1267 (1985).
Power, M. D. et al., "Nucleotide Sequence of SRV-1," Science 231, 1567 (1986).
Pearl, L. H. et al., "A Structural Model for Retroviral Proteases," 329 Nature 329, 351 (1987).
Paine, J. B., "A Convenient Synthesis of Nicotinate Esters . . . ," J. Heterocyclic Chem. 24, 351 (1987).
Azri, S. et al., "Precision-Cut Liver Slices," In Vitro Toxicology 3, 309 (1990).
Smith, P. F. et al., "Dynamic Organ Culture of Precision Liver Slices . . . ," Liver Slices for in Vitro Technology 36, 1367 (1985).
Krumdieck, C. L. et al., "A New Instrument for Rapid Preparation of Tissue slices," Anal. Biochem. 104, 118 (1980).
Chapman, D. E. et al., "Metabolism and Covalent Binding of C-toluene by Human and Rat Liver Microsomal Fractions," Drug Metabolism and Dispostion 18, 929 (1990).
Goldman, M. E. et al., "Pyridinone derivatives: Specific HIV-1 reverse transcriptase inhibitors with antiviral activity," Proc. Nat. Acad. Sci. 88, 6863 (1991).

Primary Examiner—Douglas W. Robinson
Assistant Examiner—S. Saucier
Attorney, Agent, or Firm—Roy D. Meredith; Jack L. Tribble; Paul D. Matukaitis

[57] ABSTRACT

Incubation of

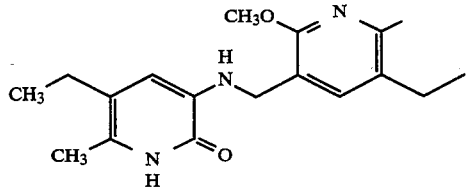

with a preparation from mammalian organ yields as biotransformation products the 5-(1-hydroxy)ethyl pyridinone analog as well as the 5-(1-hydroxy)ethyl pyridyl and the 5-(2-hydroxy)ethyl pyridyl derivatives.

3 Claims, No Drawings

METHOD OF HYDROXYLATING 3-[3-(5-ETHYL-2-METHOXY-6-METHYL-PYRIDYL)METHYL]AMINO-5-ETHYL-6-METHYL-2(1H)-PYRIDINONE WITH LIVER SLICES

This is a continuation of application Ser. No. 07/771,676, filed Oct. 4, 1991, now abandoned.

The present invention relates to a novel process for the preparation of compounds Ia, Ib, and Ic:

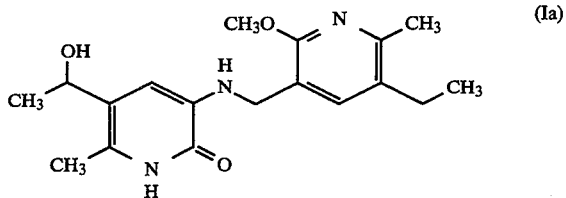

3-[3-(5-ethyl-2-methoxy-6-methylpyridyl)methyl]amino-5-(1-hydroxy)ethyl-6-methyl-2(1H)-pyridinone,

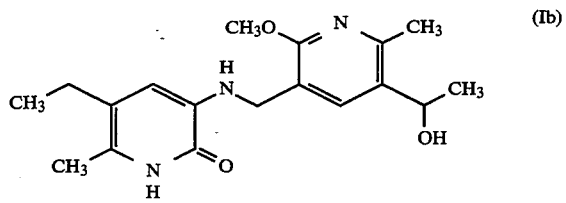

3-[3-(5-(1-hydroxy)ethyl-2-methoxy-6-methylpyridyl)methyl]amino-5-ethyl-6-methyl-2(1H)-pyridinone,

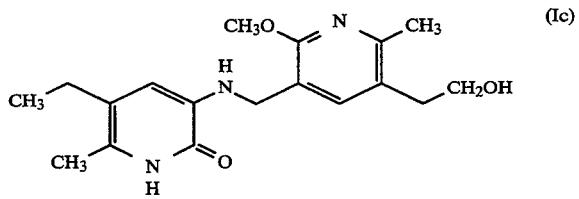

3-[3-(5-(2-hydroxy)ethyl-2-methoxy-6-methylpyridyl)methyl]amino-5-ethyl-6-methyl-2(1H)-pyridinone, comprising incubation of compound (II), an inhibitor of the reverse transcriptase encoded by human immunodeficiency virus (HIV),

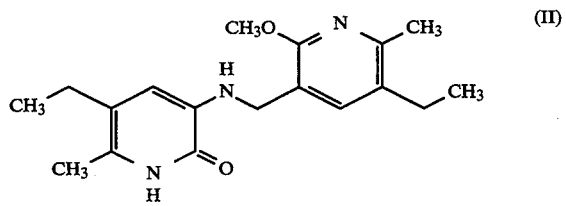

3-[3-(5-ethyl-2-methoxy-6-methylpyridyl)methyl]amino-5-ethyl-6-methyl-2(1H)-pyridinone,
with a preparation from mammalian organ. Compounds Ia, Ib, and Ic, or the pharmaceutically acceptable esters thereof inhibit the reverse transcriptase encoded by HIV and are of value in the prevention of infection by HIV, the treatment of infection by HIV and the treatment of the resulting acquired immune deficiency syndrome (AIDS).

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in vital replication. It is known that some compounds are reverse transcriptase inhibitors and are effective agents in the treatment of AIDS and similar diseases, e.g., azidothymidine or AZT.

The nucleotide sequence of HIV shows the presence of a pol gene in one open reading frame [Rather, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

The compounds prepared by the process of this invention are inhibitors of HIV reverse transcriptase. Since the compounds are metabolites, they are better adapted as pharmaceutical products. Further, the compounds of the present invention do not require bio-activation to be effective.

BRIEF DESCRIPTION OF THE INVENTION

The novel process of this invention comprises incubation of Compound II:

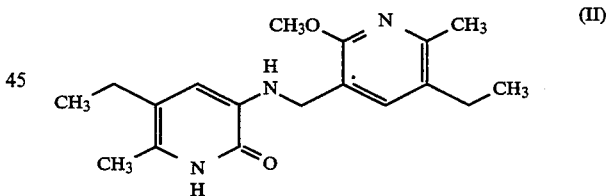

3-[3-(5-ethyl-2-methoxy-6-methylpyridyl)methyl]amino-5-ethyl-6-methyl-2(1H )-pyridinone,
with a preparation from a mammalian organ, and isolation of the resulting biotransformation products, Compounds Ia, Ib, and Ic in a conventional manner:

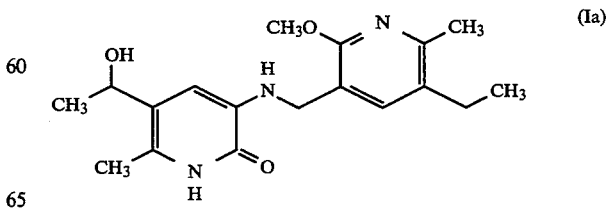

3-[3-(5-ethyl-2-methoxy-6-methylpyridyl)methyl]amino-5-(1-hydroxy)ethyl-6-methyl-2(1H)-pyridinone,

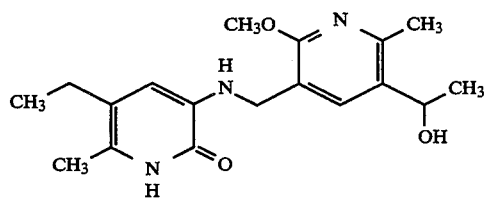

3-[3-(5-(1-hydroxy)ethyl-2-methoxy-6-methylpyridyl)-methyl]amino-5-ethyl-6-methyl-2(1H)-pyridinone,

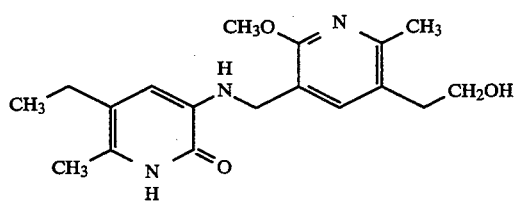

3-[3-(5-(2-hydroxy)ethyl-2-methoxy-6-methylpyridyl)-methyl]amino-5-ethyl-6-methyl-2(1H)-pyridinone.

These compounds are useful in the inhibition of HIV reverse transcriptase, the prevention of infection by HIV, the treatment of infection by HIV and in the treatment of AIDS and/or ARC, either as compounds, a pharmaceutically acceptable salt (when appropriate), hydrate, ester, pharmaceutical composition ingredient, whether or not in combination with other antivirals, anti-infectives, immunomodulators, antibiotics or vaccines.

DETAILED DESCRIPTION OF THE INVENTION AND PREFERRED EMBODIMENTS

The novel process of this invention comprises incubation of compound (II):

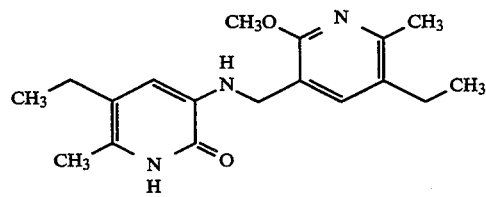

b  3-[3-(5-ethyl-2-methoxy-6-methylpyridyl)methyl]amino-5-ethyl-6-methyl-2(1H)-pyridinone,
with a preparation from mammalian organ, and isolation of the resulting biotransformation products, compounds Ia, Ib, and Ic in a conventional manner:

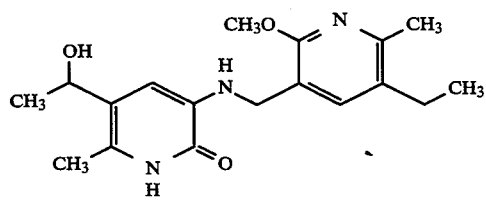

3-[3-(5-ethyl-2-methoxy-6-methylpyridyl)methyl]amino-5-(1-hydroxy)ethyl-6-methyl-2(1H)-pyridinone,

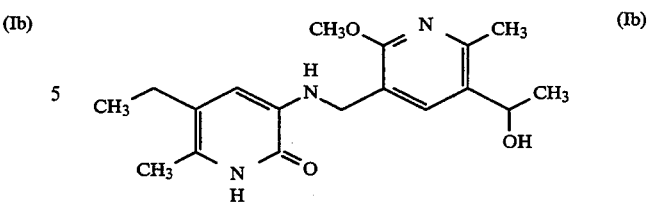

3-[3-(5-(1-hydroxy)ethyl-2-methoxy-6-methylpyridyl)-methyl]amino-5-ethyl-6-methyl-2(1H)-pyridinone,

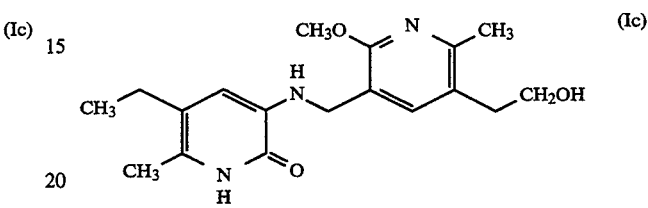

3-[3-(5-(2-hydroxy)ethyl-2-methoxy-6-methylpyridyl)-methyl]amino-5-ethyl-6-methyl-2(1H)-pyridinone.

In general, compounds Ia, Ib, and Ic can be produced by incubating an appropriate amount of substrate compound (II) with certain mammalian tissues or cell cultures in an aqueous medium suitable for enhancing the viability of the tissues or cells. Metabolites Ia, Ib, or Ic may be produced by incubation of compound (II) with a preparation from mammalian organ containing: a) preparations from surgically derived specimens including liver, kidneys, lungs and skin, both from animals and human beings; b) prenatal and gestational tissues; c) cell cultures; d) subcellular fractions like microsomes, S9 and cytosol; and/or e) purified mixed function oxidases. These metabolites could also be formed in vivo in animals and human beings. The preferred tissue for production of compounds Ia, Ib, or Ic is liver, especially rat liver slices.

The appropriate amount of tissue or cell culture to be used with a given amount of substrate compound will vary with the particular type of culture used. An appropriate ratio of substrate compound (II) to be incubated with liver tissue (mg:g, wet weight) ranges from about 1:0.3 to 1:3.0, preferably 1:2.0. When using surgically derived specimens, especially liver, the specimen is preferably cut into slices with thickness ranging from about 100$\mu$ to 1000$\mu$, and more preferably from about 250 to 400$\mu$.

Aqueous media sufficient in amount and kind to keep the tissue or cells healthy in the incubation process should be used. These media are known and available in the art of drug metabolism and include various buffers and standard culture media with or without additives. A few examples of various culture media that may be employed are Williams' Medium E, Waymouth's Medium, Dulbecco's Medium, RPMI Medium and the like. Culture media can be replaced by general buffers such as phosphate buffers. Various additives that may be used to enhance the viable life of the cells and tissues are a) serum from bovine, horse, chicken, goat, sheep, rabbit and the like; b) HEPES or MOPS; c) gentamycin; and d) insulin, for example. A preferred medium for incubation of substrate compound (II) with rat liver slices is Williams' Medium E.

The material is incubated at a temperature between 35° and 39° C., preferably 37° C., and at a pH between 7.2 and 7.6, preferably 7.4, under an atmosphere of 0% to 5% carbon dioxide in oxygen, or air. The material is incubated for a period of time necessary to complete the oxidative biotransformation as monitored by HPLC (high performance liquid chromatography), usually for a period of about four hours when incubated with rat liver slices.

The biotransformation products Ia, Ib and Ic can be isolated and purified from the incubation mixture by extraction with a conventional solvent(s) or mixtures thereof, such as methylene chloride, ethyl acetate, acetonitrile, methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred recovery method is solvent extraction, particularly using ethyl acetate. A preferred purification method involves the use of chromatography, especially HPLC, using a bonded silica gel column. Eluant mixtures for chromatography can be composed of water and an organic solvent such as methanol, acetonitrile and the like, and may optionally include a small amount of base, such as ammonium bicarbonate, or an acid, such as trifluroacetic acid, phosphoric acid, or acidic ammonium acetate. A preferred eluant is composed of acetonitrile and water containing 0.1% ammonium bicarbonate and is run through the column with a linear gradient.

A process for making esters of Ia, Ib, or Ic is also encompassed by the present invention. Such esters are those which would readily occur to the skilled artisan, and include, for example, $C_{1-4}$ alkyl esters. Also, the biotransformed compounds of this invention may have one or more chiral centers and may occur as a racemate, racemic mixture, mixture of diastereomers or enantiomers, or as an individual enantiomer, with all enantiomeric forms being included in the present invention.

The compounds of the present inventions are useful in the inhibition of HIV reverse transcriptase, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compound of this invention is useful in treating infection by HIV after suspected past exposure to HIV by, e.g., blood transfusion, organ transplant, exchange of bodily fluids, bites, accidental needle stick, or exposure to patient blood during surgery.

EXAMPLE 1

Preparation of
3-[3-(5-ethyl-2-methoxy-6-methyl-3-pyridyl)methyl-]amino-5-ethyl-6-methyl-2(1H)-pyridinone, Compound II A solution of 3-amino-5-ethyl-6-methyl-2(1H)-pyridinone (12.66 g, 83.2 mmol, see Example 2, Step B), 5-ethyl-2-methoxy-6-methylnicotinaldehyde (15.0 g, 83.2 mmol, see Example 3, Step F), and acetic acid (5 drops in methanol (83 mL) was stirred at room temperature for 18 hours under an atmosphere of nitrogen. The yellow-orange precipitate was filtered, washed with a small amount of methanol, and then dissolved in a mixture of methanol and chloroform (3:1 v/v) with warming. The resultant solution was allowed to cool back to room temperature and sodium cyanoborohydride was added until all the Schiff base was reduced. The product solution was then concentrated under vacuum. Water and chloroform were added to the residue. The aqueous layer was separated and extracted three more times with chloroform. The organic extracts were combined, dried over anhydrous sodium sulfate, filtered and concentrated under vacuum. The residue was then subjected to column chromatography on silica gel and eluted with 5% methanol in chloroform. Collection and concentration of appropriate fraction, followed by recrystallization (ethanol) yielded 10.5 g (40%) of the title compound, 165°–167° C.

Anal. Calcd. for $C_{18}H_{25}N_3O_2$: C, 68.54; H, 7.99; N, 13.32.

Found C, 69.17; H, 7.99; N, 13.36%.

EXAMPLE 2

Preparation of
3-amino-5-ethyl-6-methyl-2(1H)-pyridinone

Step A) Preparation of 5-ethyl-6-methyl-3-nitro-2-(1H)-pyridinone

A mixture of 2-ethyl-3-oxobutanal, sodium salt (7.5 g, 55 mmol), nitroacetamide (6.6 g, 63 mmol), aqueous piperidinium acetate (4.4 mL) [prepared from glacial acetic acid (42 mL), water (100 mL) and piperidine (72 mL)] in water (45 mL) was stirred at room temperature for 22 hours. The yellow precipitate was collected by filtration and air dried to yield 8.0 g (80%) of 5-ethyl-6-methyl-3-nitro-2-(1H)-pyidinone.

Step B) Preparation of 3-amino-5-ethyl-6-methyl-2-(1H)-pyridinone

A yellow solution of the 5-ethyl-6-methyl-3-nitro-2-(1H)-pyidinone (10 g, 55 mmol) in a mixture of methanol and tetrahydrofuran (100 mL, 1:1 v/v) was reduced catalytically in the presence of 7% palladium on charcoal (0.7 g ) under an atmosphere of hydrogen (50 psi) at room temperature over a period of 3.5 hours. The resultant mixture was filtered through a small pad of Celite. The filtrate was concentrated under reduced pressure (15 torr) to provide 5.7 g (68%) of the corresponding aminopyridone.

EXAMPLE 3

3-[2-(Benzoxazol-2-yl)ethyl]-5-ethyl-6-methyl-2-(1H)pyridinone

Step A: Preparation of 3-cyano-5-ethyl-6-methyl-2-(1H)-pyridinone

According to the method described in J. Heterocyclic Chem., 24, 351 (1987), a mixture of 2-ethyl-3-oxobutanal, sodium salt (37.5 g, 0.275 mmol), cyanoacetamide (25.2 g, 0.30 mol), aqueous piperidinium acetate (22 mL) [prepared from glacial acetic acid (4.2 mL), water (10 mL) and piperidine (7.2 mL)] in water (775 ml) was refluxed for four hours. Glacial acetic acid (30 ml) was added cautiously (much foaming) as the product precipitated. Upon cooling to room temperature,the product was collected by filtration, washed with cold water and air dried to yield 22.3 g (50%), m.p. 237°–240° C.

Step B: Preparation of 5-ethyl-6-methyl-2-(1H)-pyridinone-3-carboxylic acid

An initial suspension of 3-cyano-5-ethyl-6-methyl-2-(1H)-pyridinone (4.86 g, 30 mmol) in 6N HCl (100 mL) was heated at reflux for twenty hours. Upon cooling, the product crystallized and was collected by filtration, washed with cold water and air dried to yield 3.73 g (69%).

Step C: Preparation of methyl 2-chloro-5-ethyl-6-methyl nicotinate

A mixture of 5-ethyl-6-methyl-2-(1H)-pyridinone-3-carboxylic acid (3.62 g, 20 mmol) and phosphorus pentachloride (4.38 g, 21 mmol) was heated, under a nitrogen atmosphere, at 100°-120° C. for 1.5 hours. The cooled residue was diluted with chloroform (70 mL) and then methanol (15 mL) was added. After stirring for 2-16 hours, the solution was poured into ice/water. The organic layer was separated and washed successively with water, saturated aqueous $NaHCO_3$, dried ($Na_2SO_4$), filtered and the solvent evaporated. This dark amber oil was dissolved in hexane, filtered through a pad of charcoal and the solvent evaporated to yield 3.31 g (78%) of pure product as a light yellow oil.

Step D: Preparation of methyl 2-methoxy-5-ethyl-6-methylnicotinate

To a solution of sodium metal (0.55 g, 24 mmol) dissolved in anhydrous methanol (15 mL), under a nitrogen atmosphere, was added a solution of methyl 2-chloro-5-ethyl-6-methylnicotinate (3.18 g, 14.9 mmol) in dry methanol (5 mL). This solution was refluxed and monitored by tlc (thin layer chromatogram) until the starting material had been consumed (about 24 hours). The cooled mixture was diluted with diethyl ether (50 mL), washed with water, saturated aqueous $NaHCO_3$, dried ($Na_2SO_4$), filtered and the solvent evaporated to yield 2.28 g (73%) of pure product as a light yellow oil.

Step E: Preparation of 2-methoxy-3-hydroxymethyl-5-ethyl-6-methyl pyridine

To a solution of methyl 2-methoxy-5-ethyl-6-methylnicotinate (2.28 g, 10.9 mmol) in anhydrous tetrahydrofuran (50 mL), under a nitrogen atmosphere, was added cautiously lithium aluminum hydride (0.77 g, 20 mmol). After refluxing this mixture for 15-20 hours, saturated aqueous $Na_2SO_4$ was added carefully to quench the cooled reaction mixture. This mixture was diluted with more THF, dried ($Na_2SO_4$), filtered and the solvent evaporated. This residue was chased with ethanol/toluene to remove traces of water and triturated with hexane as the product slowly crystallized out to give 1.30 g (66%), mp 53°-55° C.

Step F: Preparation of 5-ethyl-2-methoxy-6-methyl nicotinaldehyde

Activated manganese dioxide (2.0 g) was added to a solution of 2-methoxy-3-hydroxymethyl-5-ethyl-6-methylpyridine (1.18 g, 6.5 mmol) in dry benzene (20 mL) and refluxed 5-10 hours. The warm suspension was filtered through a pad of anhydrous $Na_2SO_4$ and evaporated to yield 1.05 g (90%) of a viscous oil which solidified.

EXAMPLE 4

Incubation of Compound II With Rat Liver Slices.

Compound II (157.7 μM) was incubated with rat liver slices (10.17 g wet weight, 250–400 μ thick, ~1.2 cm wide) in 100 ml of Williams' Medium E at pH 7.4 and at 37° C. under an atmosphere of 95% oxygen and 5% carbon dioxide. After four hours the incubation mixture was extracted with ethyl acetate. The extract was evaporated to dryness and the residue reconstituted in methanol. The reconstitute was subjected to preparative HPLC on a reverse-phase column with an on-line UV-diode array detector. Three major metabolites—Ia, Ib and Ic—were isolated for characterization by NMR spectroscopy and mass spectrometry.

EXAMPLE 5

STRUCTURAL DETERMINATION: NMR

In vitro metabolism studies on non-labelled compound II with rat liver slices showed formation of three major products (and at least 5 minor products) based on HPLC with photodiode array-UV detection. The three major products were identified by proton NMR (500 MHz; see Table below) and mass spectrometry as resulting from α-hydroxylation of the ethyl group on the pyridinone (HPLC Peak designating compound Ia), and β- and α-hydroxylation of the ethyl group on the pyridine (designated compounds Ic and Ib, respectively).

Parent Compound II

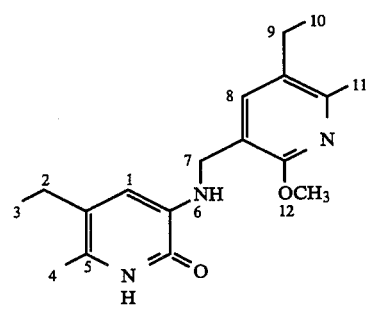

TABLE

| proton | Chemical Shift in CD$_3$CN (ppm) | | | |
| --- | --- | --- | --- | --- |
|  | II | Ia | Ic | Ib |
| 1 | 6.11 | 6.35 | 6.10 | 6.10 |
| 2 | 2.27 | 4.74 | 2.27 | 2.27 |
| 3 | 1.00 | 1.20 | 1.00 | 1.00 |
| 4 | 2.07 | 2.05 | 2.07 | 2.07 |
| 5 | 9.25 | 9.07 | 9.06 | 9.10 |
| 6 | 5.14 | 5.15 | 5.12 | 5.15 |
| 7 | 4.18 | 4.20 | 4.17 | 4.20 |
| 8 | 7.31 | 7.31 | 7.31 | 7.60 |
| 9 | 2.52 | 2.52 | 2.68 | 4.94 |
| 10 | 1.09 | 1.10 | 3.59 | 1.28 |
| 11 | 2.36 | 2.37 | 2.38 | 2.38 |
| 12 | 3.90 | 3.91 | 3.90 | 3.92 |
| 2-OH | — | 4.45 | — | — |
| 10-OH | — | — | 2.63 | — |
| 9-OH | — | — | — | 3.06? |

EXAMPLE 6

STRUCTURAL DETERMINATION: FAB/MS

High resolution mass spectrometry showed the following results:

| Compound | Measured Mass (M + H)$^+$ | Empirical Formula (M + H)$^+$ |
| --- | --- | --- |
| II | m/z 316.20270 | $C_{18}H_{26}N_3O_2$ |
| Ia | m/z 332.19502 | $C_{18}H_{26}N_3O_3$ |
| Ic | m/z 332.19716 | $C_{18}H_{26}N_3O_3$ |
| Ib | m/z 332.19743 | $C_{18}H_{26}N_3O_3$. |

The mass spectra of the metabolites indicated that they were hydroxy analogs of the parent compound.

EXAMPLE 7

REVERSE TRANSCRIPTASE ASSAY

The assay measures the incorporation of tritiated deoxyguanosine monophosphate by recombinant HIV reverse transcriptase (HIV $RT_R$) (or other RT) into acid-precipitable cDNA at the Km values of dGTP and poly r(C)•oligo d(G)$_{12-18}$. The inhibitor of the present invention inhibits this incorporation.

Thirty uL of a reaction mixture containing equal volumes of: 500 mM Tris•HCl (pH 8.2), 300 mM MgCl$_2$, 1200 mM KCl, 10 mM DTT, 400 µg/mL poly r(c)•oligo d(G) [prepared by dissolving 1.5 mg (25 U) poly r(C)•oligo d(G) in 1.5 ml sterile distilled H$_2$O and diluting to 400 µg/ml], 0.1 µCi/µl [$^3$H]dGTP, 160 µM dGTP, was added to 10 µl sterile distilled H$_2$O, and 2.5 µl of potential inhibitor. An aliquot of 10 µL of 5 nM purified HIV $RT_R$ was added to initiate the reaction. The mixture was incubated at 37° C. for 45 minutes.

After incubation is complete, the tubes were cooled in ice for 5 minutes. Ice-cold 13% TCA containing 10 mM NaPP$_i$ (200 µl) are added and the mixture incubated on ice for 30 minutes. The precipitated cDNA is removed by filtration using presoaked glass filters [TCA, NaPP$_i$]. The precipitate is then washed with 1N HCl, 10 mM NaPP$_i$.

The filter discs are then counted in a scintillation counter.

Under these conditions [dGTP] and poly r(C)•oligo d(G)$_{12-18}$ each are approximately equal to the appropriate Km value. Approximately 5–6,000 cpm of [$^3$H] GMP are incorporated into acid-precipitable material. The RT reaction is concentration- and time-dependent. DMSO (up to 5%) does not affect enzyme activity. The calculated IC$_{50}$ values for the compounds of this invention are as follows:

| Compound | IC$_{50}$(µM) |
|---|---|
| Ia | 0.195 |
| Ib | 0.390 |
| Ic | 0.250 |
| II | 0.029 |

While the foregoing specification teaches the principles of the present invention, with examples provided for the purpose of illustration, it will be understood that the practice of the invention encompasses all of the usual variations, adaptations, or modifications, as come within the scope of the following claims and its equivalents.

What is claimed is:

1. A method of preparing the compound

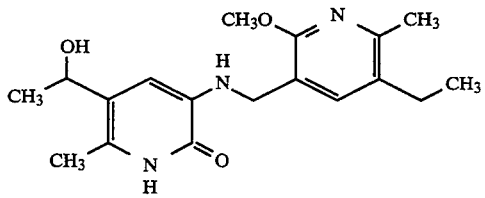

3-[3-(5-ethyl-2-methoxy-6-methylpyridyl)methyl-]amino-5-(1-hydroxy)ethyl-6-methyl-2(1H)-pyridinone, comprising the steps of
 (a) providing a quantity of 3-[3-(5-ethyl-2-methoxy-6-methylpyridyl)methyl]amino-5-ethyl-6-methyl-2(1H)-pyridinone,
 (b) incubating the compound of step (a) with rat liver slices, and
 (c) isolating the compound Ia.

2. A method of preparing the compound

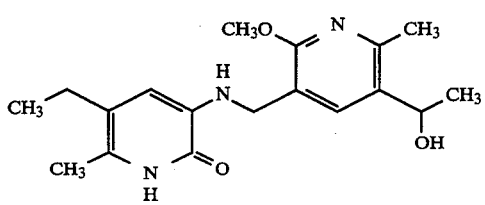

3-[3-(5-(1-hydroxy)ethyl-2-methoxy-6-methylpyridyl)methyl]amino-5-ethyl-6-methyl-2(1H)-pyridinone, comprising the steps of
 (a) providing a quantity of 3-[3-(5-ethyl-2-methoxy-6-methylpyridyl)methyl]amino-5-ethyl-6-methyl-2(1H)-pyridinone,
 (b) incubating the compound of step (a) with rat liver slices, and
 (c) isolating the compound Ib.

3. A method of preparing the compound

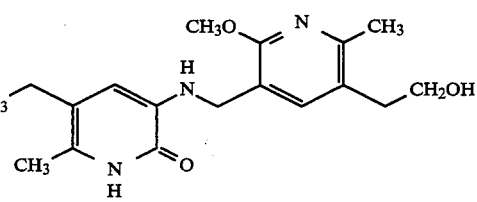

3-[3-(5-(2-hydroxy)ethyl-2-methoxy-6-methylpyridyl)methyl]amino-5-ethyl-6-methyl-2(1H)-pyridinone, comprising the steps of
 (a) providing a quantity of 3-[3-(5-ethyl-2-methoxy-6-methylpyridyl)methyl]amino-5-ethyl-6-methyl-2(1H)-pyridinone,
 (b) incubating the compound of step (a) with rat liver slices, and
 (c) isolating the compound Ic.

* * * * *